(12) United States Patent
Van Der Heide et al.

(10) Patent No.: US 7,342,141 B2
(45) Date of Patent: Mar. 11, 2008

(54) PROCESS FOR THE PREPARATION OF ALKANEDIOL

(75) Inventors: Evert Van Der Heide, Amsterdam (NL); Cornelis Leonardus Maria Vrouwenvelder, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/678,009

(22) Filed: Feb. 22, 2007

(65) Prior Publication Data

US 2007/0203373 A1   Aug. 30, 2007

(30) Foreign Application Priority Data

Feb. 22, 2006   (EP)   .................. 06110248

(51) Int. Cl.
  *C07C 29/159*   (2006.01)
  *C07C 29/15*   (2006.01)
(52) U.S. Cl. ...................... 568/867; 568/866
(58) Field of Classification Search ................. 568/867, 568/866
  See application file for complete search history.

(56) References Cited

U.S. PATENT DOCUMENTS

| | | | |
|---|---|---|---|
| 2,994,705 A | 8/1961 | Crosby et al. | 260/340.2 |
| 3,803,201 A | 4/1974 | Glipin et al. | 260/463 |
| 4,314,945 A | 2/1982 | McMullen et al. | 260/340.2 |
| 4,434,105 A | 2/1984 | Buysch et al. | 260/463 |
| 4,508,927 A | 4/1985 | Bhise et al. | 568/858 |
| 4,691,041 A | 9/1987 | Duranleeau et al. | 558/277 |
| 5,153,333 A | 10/1992 | Schubert et al. | 549/230 |
| 5,231,212 A | 7/1993 | Buysch et al. | 558/277 |
| 5,359,118 A | 10/1994 | Wagner et al. | 558/277 |
| 5,426,207 A | 6/1995 | Harrison et al. | 558/274 |
| 5,449,791 A | 9/1995 | Wagner et al. | 549/230 |
| 5,455,368 A | 10/1995 | Janisch et al. | 58/277 |
| 5,508,442 A | 4/1996 | Wagner et al. | 549/228 |
| 5,847,189 A | 12/1998 | Tojo et al. | 558/277 |
| 6,156,160 A | 12/2000 | Marquis et al. | 203/29 |
| 6,187,972 B1 | 2/2001 | Kawabe et al. | 568/858 |
| 6,294,684 B1 | 9/2001 | de Bruin et al. | 558/274 |
| 6,380,419 B2 | 4/2002 | Kawabe | 558/277 |
| 6,392,078 B1 | 5/2002 | Ryu et al. | 558/277 |
| 6,407,279 B1 | 6/2002 | Buchanana et al. | 558/227 |
| 6,479,689 B1 | 11/2002 | Tojo et al. | 558/277 |
| 6,573,396 B2 | 6/2003 | Buchanan et al. | 558/277 |
| 6,774,256 B2 | 8/2004 | Schlosberg et al. | 558/277 |

FOREIGN PATENT DOCUMENTS

| | | |
|---|---|---|
| CN | 1060091 | 4/1992 |
| CN | 1102826 | 5/1995 |
| CN | 1528735 | 9/2004 |
| EP | 0297647 | 6/1788 |
| EP | 0001082 | 3/1979 |
| EP | 0274953 | 7/1988 |
| EP | 0180387 | 5/1990 |
| EP | 0583789 | 2/1994 |
| EP | 0776890 | 1/2001 |
| EP | 1174406 | 1/2002 |
| EP | 0119840 | 9/2004 |
| JP | 55-64550 | 5/1980 |
| JP | 61-291545 | 12/1986 |
| JP | 2-212456 | 8/1990 |
| JP | 2003-81893 | 3/1993 |
| JP | 9-183744 | 7/1997 |
| JP | 2000-005503 | 1/2000 |
| JP | 2000-113144 | 4/2003 |
| JP | 2003-155264 | 5/2003 |
| JP | 2003-342236 | 12/2003 |
| WO | WO9957108 | 11/1999 |
| WO | WO03006418 | 1/2003 |
| WO | WO03082797 | 10/2003 |
| WO | WO2004056793 | 7/2004 |
| WO | WO2005003113 | 1/2005 |
| WO | WO2005051939 | 6/2005 |

*Primary Examiner*—Elvis O. Price

(57) ABSTRACT

The invention provides a process for the preparation of alkanediol comprising the steps:
  (i) contacting alkylene oxide with carbon dioxide in the presence of a carbonation catalyst to obtain a reaction mixture containing alkylene carbonate at a reaction temperature of from 100 to 200° C.;
  (ii) contacting the reaction mixture obtained in step (i) with R—OH, in which R is hydrogen or an alkyl group in the presence of a catalyst to obtain a second reaction mixture containing alkanediol and $R_2CO_3$;
  (iii) subjecting the second reaction mixture containing alkanediol and $R_2CO_3$ to a separation step to yield a crude alkanediol stream, which is subjected to distillation to yield a purified stream of alkanediol as the bottom stream;
  (iv) subjecting the purified stream of alkanediol obtained in step (iii) to further distillation to obtain a second bottom stream containing a mixture of alkanediol, heavy components, and optionally carbonation catalyst, and a top stream containing high purity alkanediol;
wherein at least part of the reaction mixture obtained in step (i) is used for heat exchange with at least part of the crude alkanediol stream and/or with at least part of the purified alkanediol stream.

10 Claims, No Drawings

US 7,342,141 B2

PROCESS FOR THE PREPARATION OF ALKANEDIOL

This application claims the benefit of European Patent Application 06110248.9 filed Feb. 22, 2006 which is incorporated herein by reference.

FIELD OF THE INVENTION

The present invention relates to a process for preparing alkanediol from alkylene carbonate under heat recovery.

BACKGROUND

It is well known to convert alkylene oxide into a cyclic alkylene carbonate in the presence of a suitable catalyst. Such processes have been described for example in U.S. Pat. No. 4,508,927 and U.S. Pat. No. 5,508,442. These patents describe processes in which an alkylene oxide is reacted with carbon dioxide in the presence of a catalyst to form the cyclic alkylene carbonate. The catalyst can be an organic phosphonium halide as described in U.S. Pat. No. 4,508,927, a metal halide as described in U.S. Pat. No. 5,508,442, or an organic trisubstituted phosphine as described in Japanese patent application No. 73022702.

A process for hydrolyzing cyclic alkylene carbonates to produce a diol and carbon dioxide, more specifically to produce 1,2-propanediol, has been disclosed in WO-A 2004/056793. This reference describes a process for the preparation of 1,2-propanediol from propylene oxide, which process comprises: (a) contacting propylene oxide with carbon dioxide in the presence of a homogeneous phosphorus comprising catalyst to obtain propylene carbonate, (b) optionally removing at least part of the carbon dioxide, (c) adding water to the reaction product comprising propylene carbonate and phosphorus comprising catalyst and contacting the mixture with a heterogeneous catalyst to obtain 1,2-propanediol in combination with dialkyl carbonate and/or carbon dioxide, and (d) separating 1,2-propanediol from the reaction product obtained.

This process requires a considerable amount of energy. It would therefore be an advancement in the art to obtain an improvement of the method of the above process, to more efficiently control the energy balance of the process.

SUMMARY OF THE INVENTION

The present invention provides a process for the preparation of alkanediol comprising:
(i) contacting alkylene oxide with carbon dioxide in the presence of a carbonation catalyst to obtain a reaction mixture containing alkylene carbonate at a reaction temperature of from 100 to 200° C.;
(ii) contacting the reaction mixture obtained in step (i) with R—OH, in which R is hydrogen or an alkyl group in the presence of a catalyst to obtain a second reaction mixture containing alkanediol and $R_2CO_3$;
(iii) subjecting the second reaction mixture containing alkanediol and $R_2CO_3$ to a separation step to yield a crude alkanediol stream, which is subjected to distillation to yield a purified stream of alkanediol as a bottom stream;
(iv) subjecting the purified stream of alkanediol obtained in step (iii) to further distillation to obtain a second bottom stream containing a mixture of alkanediol, heavy components, and optionally carbonation catalyst, and a top stream containing high purity alkanediol;

wherein at least part of the reaction mixture obtained in step (i) is used for heat exchange with at least part of the crude alkanediol stream and/or with at least part of the purified alkanediol stream.

DETAILED DESCRIPTION

The process of the present invention is suitable for the preparation of $C_2$-$C_6$ alkanediols, more especially 1,2-propanediol and 1,2-ethanediol, from the corresponding $C_3$-$C_7$ alkylene carbonates which are prepared by reacting the corresponding $C_2$-$C_6$ alkylene oxide with carbon dioxide. Where 1,2-ethanediol is to be prepared, the alkylene oxide to be used in step (i) of the present process is ethylene oxide and the alkylene carbonate obtained in step (i) is ethylene carbonate. Preferably, the process of the present invention is used for the preparation of 1,2-propanediol. In the latter case, the alkylene oxide to be used in step (i) is propylene oxide and the alkylene carbonate obtained in step (i) is propylene carbonate.

In step (i) of the invention alkylene carbonate is prepared from alkylene oxide and carbon dioxide. Alkylene carbonate can be obtained by methods known in the art. For instance, propylene oxide is contacted with carbon dioxide in the presence of a carbonation catalyst, such as a homogenous phosphorus-containing catalyst or metal halide catalysts such as disclosed in U.S. Pat. No. 5,508,442. Other homogeneous carbonation catalysts are well known in the art and have been e.g. described in U.S. Pat. No. 4,508,927 and Japanese patent application No. 73022702.

The carbon dioxide can be either pure carbon dioxide or carbon dioxide comprising further compounds. Since in one embodiment of the present process in which R is hydrogen, $R_2CO_3$ will decompose into water and carbon dioxide. It is especially suitable to use such carbon dioxide. Carbon dioxide is produced in the reaction of the alkylene carbonate with water. Therefore, it is especially attractive to separate carbon dioxide in step (ii) of the process. The carbon dioxide separated as such or after having been purified, can be recycled to step (i) of making alkylene carbonate from alkylene oxide. The extent to which the carbon dioxide is purified depends on the nature and the amounts of contaminants present in the carbon dioxide. These again depend on the exact reaction conditions and purification steps of the process.

Alkylene oxide, e.g. propylene oxide, is reacted with carbon dioxide at operating conditions which are well known to be suitable. Such process conditions will generally comprise a temperature of from 100 to 200° C., more specifically 120 to 190° C., and a pressure of at least $5 \times 10^5$ $N/m^2$, more specifically a pressure of from 5 to $100 \times 10^5$ $N/m^2$, most specifically of from 10 to $30 \times 10^5$ $N/m^2$.

The advantageous results of the present invention are obtainable by the selection of the reaction temperatures of step (i) and the heat exchange of the relatively hot reaction mixture obtained in step (i) with the relatively cold streams to be distilled in steps (iii) and/or (iv) (i.e., the crude alkanediol stream and/or the purified alkanediol stream). This method is very advantageous for performing the process at low energy costs. Since low temperature heat cannot be integrated in other parts of the process and high temperature operations are limited by the desired selectivity of the reactor, this process has a further advantage over the prior art processes. In a preferred embodiment the inlet temperature is from 120 to 170° C. and the outlet temperature from 150 to 190° C., provided that the inlet temperature is lower than the outlet temperature.

The heat exchange can be obtained by liquid-liquid heat exchange or by evaporating heat exchange. More preferred, heat exchange can be obtained by evaporating heat exchange, which limits the maximum temperature of the heat recovered to below the lowest temperature in the heat exchanger. The temperature delta over the heat exchanger is determined by the recycle ratio, which preferably is between 5 and 350. By applying a ratio of about 20 the heat delta over the heat exchanger is around 180 to 150° C., which has the additional advantage that the heat can be integrated by means of an evaporating medium, such as steam, with other units. Suitable units include a water distillation column and a catalyst concentration unit, which both operate at about 120° C. Apart from the possibility of an external heat exchanger, there is the possibility of heat exchange internally in the reactor, for instance, by using a hollow spiral filled with a liquid of with an evaporating fluid.

The heat exchange is preferably carried out on the entire crude alkanediol stream. This has the advantage that there no additional heating measures need to be taken. The skilled person will realise that the energy content in the reaction mixture is generally sufficient to heat this stream. Therefore this stream is particularly suitable for being heated in the present process. This is the more so in the embodiment where R is hydrogen. Then there is already a separation of carbon dioxide resulting from the decomposition of $H_2CO_3$.

The reaction mixture of step (i) is contacted with a hydroxyl-group containing compound of formula R—OH. R can be hydrogen, so that R—OH constitutes water. R can also be an alkyl group so that R—OH constitutes an alkanol. Suitable alkanols include $C_{1-4}$ alkanols. Particularly suitable are methanol, ethanol and isopropanol. Preferred alkanols are methanol and ethanol.

If R is hydrogen the catalyst in step (ii) is suitably a hydrolysis catalyst. The hydrolysis catalysts for use in step (ii) of the present invention are suitably heterogeneous catalysts that can catalyze the hydrolysis reaction of water, and which are well known in the art. Examples of such catalysts comprise solid inorganic compounds such as alumina, silica-alumina, alumina carrying a copper compound, silica-alumina carrying a copper compound, silica-magnesia, aluminosilicate, gallium silicate, zeolites, metal-exchanged zeolites, ammonium-exchanged zeolites, zinc on a support, lanthanum on a support, a mixture of aluminium and magnesium hydroxide and oxide, and ion-exchange resins. Preferably, the heterogeneous catalyst employed in step (ii) is chosen from the group consisting of a mixture of aluminium and magnesium hydroxide or oxide, zinc on a support, lanthanum on a support, and alumina.

A catalyst which is preferably used consists of alumina. Preferably, the alumina is gamma-alumina. Surprisingly, it was found that the alumina catalyst is especially preferred in the present invention. Carbon dioxide is released when the alkylene carbonate reacts with water and carbon dioxide is well known to cause problems if present with a basic or amphoteric catalyst. It was observed that the activity and selectivity of the alumina catalyst remained high even if a substantial amount of carbon dioxide was present such as a carbon dioxide partial pressure of from 5 to $50 \times 10^5$ N/m², more specifically of from 7 to $40 \times 10^5$ N/m², most specifically of from 10 to $30 \times 10^5$ N/m².

In a preferred embodiment step (ii) is performed in two stages. Step (ii) then comprises (ii-a) contacting alkylene carbonate with water in the presence of a hydrolysis catalyst to obtain a reaction mixture comprising alkanediol and $H_2CO_3$ which decomposes into carbon dioxide and water, and subsequently removing carbon dioxide from the reaction mixture obtained, and (ii-b) contacting at least part of the reaction mixture obtained in step (ii-a) with further hydrolysis catalyst and optionally adding further water.

When R is an alkyl group the catalyst of step (ii) is preferably a transesterification catalyst. Suitable catalysts have been described in e.g., U.S. Pat. No. 5,359,118, and include hydrides, oxides, alcoholates, amides or salts of alkali metals, i.e. lithium, sodium, potassium, rubidium and cesium. It is advantageous to use the alcoholate of the alkanol that is being used. Such alcoholates can be added as such or formed in situ. Other suitable catalysts have been described in EP-274 953, U.S. Pat. No. 3,803,201, EP-A 1082 and EP-A 180 387.

Water or alkanol is added to the reaction product comprising the alkylene carbonate, and the process is preferably carried out at a temperature of from 50 to 300° C., preferably of from 80 to 250° C., more specifically of from 100 to 200° C. The pressure can vary widely, and preferably is at most $50 \times 10^5$ N/m², more specifically at most $30 \times 10^5$ N/m².

The reaction mixture containing alkanediol and $R_2CO_3$ is subjected to a separation treatment in step (iii). When R is hydrogen carbon dioxide is formed and this is preferably removed in an intermediate stage. Preferably the carbon dioxide is removed by flash distillation. That results in a remaining stream containing alkanediol and water. This stream and reaction mixtures when R is an alkyl group are considered the crude alkanediol stream that is subjected to distillation in step (iii). This stream is subjected to distillation resulting in a bottom stream comprising the purified alkanediol and a bottom stream that either comprises water or dialkyl carbonate with unreacted alkanol, if any.

This distillation is particularly useful, as in the case 1,2-propanediol is prepared, the reaction mixture may comprise also acetaldehyde, propylene oxide, and propionaldehyde. These products may be formed as by-products in the reaction. In this way these low-boiling components are removed from the process, which prevents build-up or undesired side reactions of these components.

The purified alkanediol separated as the bottom stream is subsequently further purified by distillation. This distillation is meant to further purify the stream and free it from heavier compounds. A well known by-product in the manufacture of 1,2-propanediol is dipropylene glycol. The latter can be removed relatively easily by distillation. The high purity 1,2-propanediol is then recovered as the top stream in this distillation.

The carbonation catalyst which is present in the crude reaction mixture of step (i), can be separated off from the reaction mixture by the distillation in step (iv), at least part of which catalyst can be recycled for use in making the alkylene carbonate. The carbonation catalyst can be recycled in combination with further compounds either added to or formed in the process according to the present invention. Preferably, the catalyst will be recycled while being dissolved in alkanediol.

It was found that the presence of a solvent can be advantageous in the process according to the present invention. A protic solvent was found to reduce decomposition of the carbonation catalyst. Alkanediol, e.g. 1,2-propanediol, was found to be an especially advantageous solvent. The solvent is preferably present during the whole process such as in the carbonation step (i), conversion step (ii) and separation step (iii) and/or (iv).

The invention claimed is:

1. A process for the preparation of alkanediol comprising:
  (i) contacting alkylene oxide with carbon dioxide in the presence of a carbonation catalyst to obtain a reaction mixture containing alkylene carbonate at a reaction temperature of from 100 to 200° C.;

(ii) contacting the reaction mixture obtained in step (i) with R—OH, in which R is hydrogen or an alkyl group in the presence of a catalyst to obtain a second reaction mixture containing alkanediol and $R_2CO_3$;

(iii) subjecting the second reaction mixture containing alkanediol and $R_2CO_3$ to a separation step to yield a crude alkanediol stream, which is subjected to distillation to yield a purified stream of alkanediol as a bottom stream;

(iv) subjecting the purified stream of alkanediol obtained in step (iii) to further distillation to obtain a second bottom stream containing a mixture of alkanediol, heavy components, and optionally carbonation catalyst, and a top stream containing high purity alkanediol;

wherein at least part of the reaction mixture obtained in step (i) is used for heat exchange with at least part of the crude alkanediol stream or with at least part of the purified alkanediol stream.

2. A process according to claim 1, wherein the reaction mixture obtained in step (i) is used for heat exchange with both at least part of the crude alkanediol stream and at least part of the purified alkanediol stream.

3. A process according to claim 1, wherein a homogeneous carbonation catalyst is applied in step (i).

4. A process according to claim 1, wherein the carbonation catalyst of step (i) is a tetraalkyl phosphonium bromide catalyst.

5. A process according to claim 1, wherein part of the carbonation catalyst recovered in step (iv) is recycled.

6. A process according to claim 1, wherein in step (i) an inlet temperature of from 120 to 170° C. and an outlet temperature of from 150 to 190° C. is used, provided that the inlet temperature is lower than the outlet temperature.

7. A process according to claim 1, wherein the alkylene oxide is a $C_2$-$C_6$ alkylene oxide.

8. A process according to claim 7, wherein the $C_2$-$C_6$ alkylene oxide is ethylene oxide or propylene oxide.

9. A process according to claim 7, wherein the $C_2$-$C_6$ alkylene oxide is ethylene oxide, the alkylene carbonate is ethylene carbonate and the alkanediol is 1,2-ethanediol.

10. A process according to claim 7, wherein the $C_2$-$C_6$ alkylene oxide is propylene oxide, the alkylene carbonate is propylene carbonate and the alkanediol is 1,2-propanediol.

* * * * *